United States Patent [19]

Horwitz et al.

[11] Patent Number: 5,023,173

[45] Date of Patent: Jun. 11, 1991

[54] DEVICE FOR ASSESSING NEMATODE VITALITY AND METHOD FOR USING SAME

[75] Inventors: Arnold Horwitz, Los Angeles; Changtung P. Chang, Chatsworth, both of Calif.

[73] Assignee: Xoma Corporation, Berkeley, Calif.

[21] Appl. No.: 918,446

[22] Filed: Oct. 14, 1986

[51] Int. Cl.$^5$ .......................... C12Q 1/02; C12N 1/00
[52] U.S. Cl. ..................................... 435/29; 435/243; 435/244; 435/260; 435/297; 435/299; 435/810; 422/61; 424/84
[58] Field of Search ................ 435/29, 243, 244, 260, 435/297, 299, 810, 34; 422/61; 424/84

[56] References Cited

PUBLICATIONS

Hough, A., et al., *J. Nematol.*, 7:221–9, (1975).
Fenwick, D. W., *Trop. Agric., Trin.*, 25:125–6, (1968).
Spurr, H. W., et al., *Plant Dis. Rep.*, 50:424–5, (1966).
DiSanzo, C. P., *J. Nematol.*, 5:22–7, (1973).
Yu, C. C., et al., *J. Arg. Food Chem.*, 29:537–40, (1973).
Ward, S. W., *Proc. Nat. Acad. Sci.*, 70:817–21, (1973).
Bolan, J., et al., *Nematologica*, 22:306–11, (1976).
Jansson, H. B., et al., *J. Gen. Microbiol.*, 112:89–93, (1979).
Schmidt, J., et al., *Environ. Entomol.*, 7:605–7, (1978).
Dusenberg, D. B., *J. Nematol.*, 15:168–73, (1983).
Prot, J. C., *Rev. Nematol.*, 1:21–6, 135–42, (1978); 2:11–16, (1979).
Jansson, H. B., et al., *J. Gen. Microbiol.*, 129:1121–1126, (1983).
Papademetriou et al., *J. Chem. Ecol.*, 9:387–396, (1983).
Jeyaprakash, A., et al., *Exper. Panisitol.*, 59:90–97, (1985).
Zuckerman, B. M., et al., *Ann. Rev. Phytopathol.*, 222:95–113, (1984).

*Primary Examiner*—Esther L. Kepplinger
*Assistant Examiner*—Toni R. Scheiner
*Attorney, Agent, or Firm*—Sterne, Kessler, Goldstein & Fox

[57] ABSTRACT

The present invention relates to a method and device for the in vitro testing of potential nematicidal and nematistatic agents, comprising treatment of nematodes with test substances, followed by assessment of the ability of the treated nematodes to move through a chemattractant gradient set up on a coated solid support, said coating comprising a gellable polymeric substrate incorporating a stabilizing agent.

18 Claims, 4 Drawing Sheets

DEVICE FOR ASSESSING NEMATODE VITALITY AND METHOD FOR USING SAME

BACKGROUND OF THE INVENTION

1. Field of the Invention

This invention is directed to a device for assessing the vitality of nematodes as a measure of the efficacy of potential nematicidal and nematistatic agents.

The assay device comprises a solid support coated with a gellable polymer intimately mixed with particular chemicals that serve to stabilize the assay. Included in the device are disks impregnated with a particular chemical that is an attractant for nematodes. Included in the invention are methods for using the aforementioned device in chemotaxis assays, such assays being useful for assessing the efficacy of particular compounds as nematicidal or nematistatic agents.

2. Brief Description of the Background Art

The invasion of plant roots by parasitic nematodes leads to destruction of the plant. This is a serious problem in the agricultural industry world wide. For example, the genus Meloidoqvne can infect more than 2000 different species of plants R. S. Hussey, *Advanced Treatise on Meloidogyne*, vol. 1, North Carolina State Univ/Graphics, Raleigh, N.C., 1985.

It is well known that the invasion of host cells is preceded by the accumulation of plant-parasitic nematodes around plant roots. H. B. Jansson et al., *J. Gen. Microbiol.* 112:89 (1979). It has long been recognized that one approach to preventing invasion of plant roots by nematodes is to interrupt the mechanisms of such accumulation.

It is recognized that plant-parasitic nematodes utilize specific recognition mechanisms for finding their hosts and prey in the soil. The general consensus is that, in nematodes, the primary food-finding mechanisms are governed by chemotactic factors emanating from the host. This process, which is called chemotaxis, mediates movement toward or away from chemical gradients. In no cases known to the inventors have the chemattractants emanating from plants or microorganisms been isolated and identified. Other stimuli, such as thermal, vibratory or tactile stimuli are believed to play minor roles, if any, in food-finding behavior. N. A. Croll, et al., in *The Behavior of Nematodes: Their Activity, Census, and Responses*, Edward Arnold, Publisher, London, 1970; B.M. Zuckerman, et al., *Ann. Rev. Phytopathol.* 22:95–113 (1984).

There is no direct evidence on the manner in which reception of chemotactic signals leads to an oriented response, but a recently proposed hypothesis on nematode chemoreception speculates that carbohydrates exuded by chemosensory sensillae bind to the cuticle glycocalyx and thereafter interact with the chemotactic factors, and thereby play a role in chemoreception. B. M. Zuckerman, 1984 supra. Another hypothesis speculates that, following binding of platn chematractants to receptors in the sensory process, there results an influx of both sodium and calcium ions via ion pumps, thereby causing the generation of action potentials. K. A. Wright, *J. Nematol.* 15:151–158 (1983).

At present parasitic nematodes are attacked by chemical agents with nematicidal or nematistatic properties, in order to prevent their invastion of plant roots. The commonly used compounds are toxic, not only to plant parasitic nematodes, but to animals (including man) as well.

For example, one of the o-(methylcarbamoyl) oximes, aldicarb (Temik ®10G Union Carbide), is registered for use on several crops for the control of insect and nematode pests. The nematicidal properties of aldicarb against the root-knot nematode *M. incognita* were first described by Spurr, et al., (*Plant Dis. Rep.* 50:424–5 (1966)).

The nematicides carbofuran (C. P. DiSanzo, *J. Nematol* 5:22-7 (1973) and carbaryl (D. W. Fenwick, *Tropic Agric. Trinidad* 25:125–16 (1968)) appear to interfere with the orientation that is necessary for survival of plant parasitic nematodes.

The possibility of intervening in the detection by nematodes of chemotactic signals produced by their hosts offers attractive options for novel and non-environmentally hazardous control of plant parasitic nematodes. The development of such methods of control, as well as the discovery of new nematicidal and nematistatic agents that are more selectively toxic for nematodes, requires rapid screening procedures to allow evaluation of large numbers of potential nematicidal or nematistatic compounds. Field testing procedures are incompatible with such mass screening programs since they are cumbersome, expensive and potentially hazardous. Thus, there is a need for a rapid, reproducible, inexpensive and safe in vitro assay method for screening the effects of a large variety of substances on nematode vitality.

Many researchers have utilized nematode movement as a criterion for in vitro screening of nematicidal and nematistatic compounds. Nematodes exposed to a toxicant are classified as either motile or non-motile. Lack of motility often is equated with inability to infect or with death, and the potency of a candidate compound is thereupon evaluated. A. Hough et al., *J. Nematol.* 7:221–229 (1975).

One complication of such assays is that under laboratory conditions, nematodes exposed to low concentrations of a toxicant may recover and become active when the toxicant is removed. For example, the in vitro evaluation of various nonfumigant nematicides with cholinesterase-inhibiting properties can be misleading when their action is assessed by nematode motility tests which involve removal of the toxicant prior to assay. Furthermore, cholinesterase-inhibiting toxicants exhibit reversible reaction with the substrate, and treated nematodes often recover fully after the toxicant is removed. C. C. Yu et al., *J. Agric. Food Chem.* 25:537–540 (1972).

An additional complication to in vitro assays is that many organophosphates and carbamates will kill at very high doses. It is believed that the mode of action of sublethal doses of these compounds is nematistatic, and it is known that intoxication with carbamate nematicides is reversible at sublethal dosages. A. Hough, 1975, supra.

Thus, there is need for a reproducible in vitro assay method that is sufficiently rapid so as to obviate the complications of reversibility of the toxic effects of some nematicidal and nematistatic agents.

Assays employed in studies of chemotactic agents are potentially suitable for the rapid in vitro assessment of the potential of candidate nematicides and nematistatic agents. Nematode chemotaxis assay methods and devices are disclosed by S. W. Ward (*Proc. Nat. Acad. Sci.* 70:817–21 (1973)), J. Balan et al., (*Nematologica* 22:306–11 (1976)), J.-C. Prot (*Rev. Nematol.* 1:21–6, 135–142 (1978); (*Rev. Nematol.* 2:11–21 (1979)), H.-B. Jansson, et al.,(*J. Gen. Microbiol.* 112:89–93 (1979)) and J. Schmidt, et al. (*Environ. Entomol.* 7:605–7(1978)), and are reviewed by D. B. Dusenbery (*J. Nematol* 15:168–173 (1983)). All devices, except that of Prot supra, comprise Petri dishes coated with a layer of agar, agarose or Sephadex, the material of the coating being suspended initially in either sterile water or water-based HEPES buffer containing a detergent. Generally, the chemattractant in a suitable solvent is placed upon the surface of the coating at a prescribed location. The point of application of the chemattractant is usually covered with a disc of paper or agar. During a diffusion period of from 24 to 48 hours, gradients of the chemattractant are formed in the coating. A water or buffer control is applied to another site on the coating. Thereafter, a suspension of nematodes is placed at an appropriate site on the plate, and movement of nematodes toward the attractant is followed.

The device of Prot supra comprises a U-tube containing in both arms a continuous column of agar. The method comprises the addition of a chemattractant to one arm of the tube, and the formation of a gradient during a 48-hour diffusion period; water is added to the other arm as a control. Thereafter, nematodes are introduced into the bottom center of the agar column, and the number of nematodes moving to the chemattractant is determined and compared to the number moving to the control.

In spite of these methods and devices, it would still be useful to provide improved devices, and methods for using same, that aid in rapidly assessing the efficacy of large numbers of potential nematicidal and nematistatic agents in coated-plate motility assay systems that are based upon the principle of chemotaxis. Furthermore, the identification and use of specific nematode chemattractants in such assay systems may permit the discovery or development of new compounds which offer greater selectivity for plant parasitic nematodes and at the same time less toxicity for beneficial insects, as well as for animals and man.

SUMMARY OF THE INVENTION

The present invention is directed to a coated solid support for the assay of vitality and motility of nematodes. The present invention is also directed to in vitro methods for using the aforementioned device to assess the potential of chemicals as nematicidal or nematistatic agents. The in vitro assay is rapid, as compared to field studies with plants, is highly reproduceable, is simple to set up, and is amenable to scale-up. Inclusion of assay stabilizing (i.e., anti-reversibility) agents into the material with which the solid support is coated provides great reliability to the assay.

The device of the invention comprises a solid support, including but not limited to, glass or plastic able polymers include, but are not limited to, agar, agarose, and dextrans. Gellable polymers are inti mately mixed with chemicals constituting particular assay stabilizing agents.

At appropriate sites on the coated solid supports are placed blocks or discs of agar intimately mixed incubated for a time sufficient to form a gradient of chemattractants surrounding the agar block or disc.

Methods for using the aforementioned device to assess the efficacy of potential nematicidal and nematistatic agents comprise contacting a suspension of nematodes with a solution of the aforementioned agent under appropriate conditions of time, temperature and shaking, then applying a small aliquot of the suspension of treated nematodes to the afore-described coated support at an appropriate distance from the chemattractant gradients. After allowing the liquid to dry, the movement of nematodes toward the chemattractant gradients is followed qualitatively and quantitatively.

These aspects of the invention provide multi-step protocols that are applicable to all potential nematicidal or nematistatic agents, regardless of their chemical nature, thus having the advantage of offering uniformity of materials for any desired assay. The procedures are applicable generally with only minor modifications or adjustments being required for any specific anti-nematode agent or any particular genus of nematode. The relative potencies of different liably compared.

The assay stabilizing agents employed have the advantage of producing great reliability and reproducibility to the assay for motility and viability of treated nematodes. These assay stabilizing agents also have the advantage of being suitable for use with a variety of chemattractant salts such as are found in soils surrounding plant roots.

DESCRIPTION OF THE PREFERRED EMBODIMENTS

Figure 1:
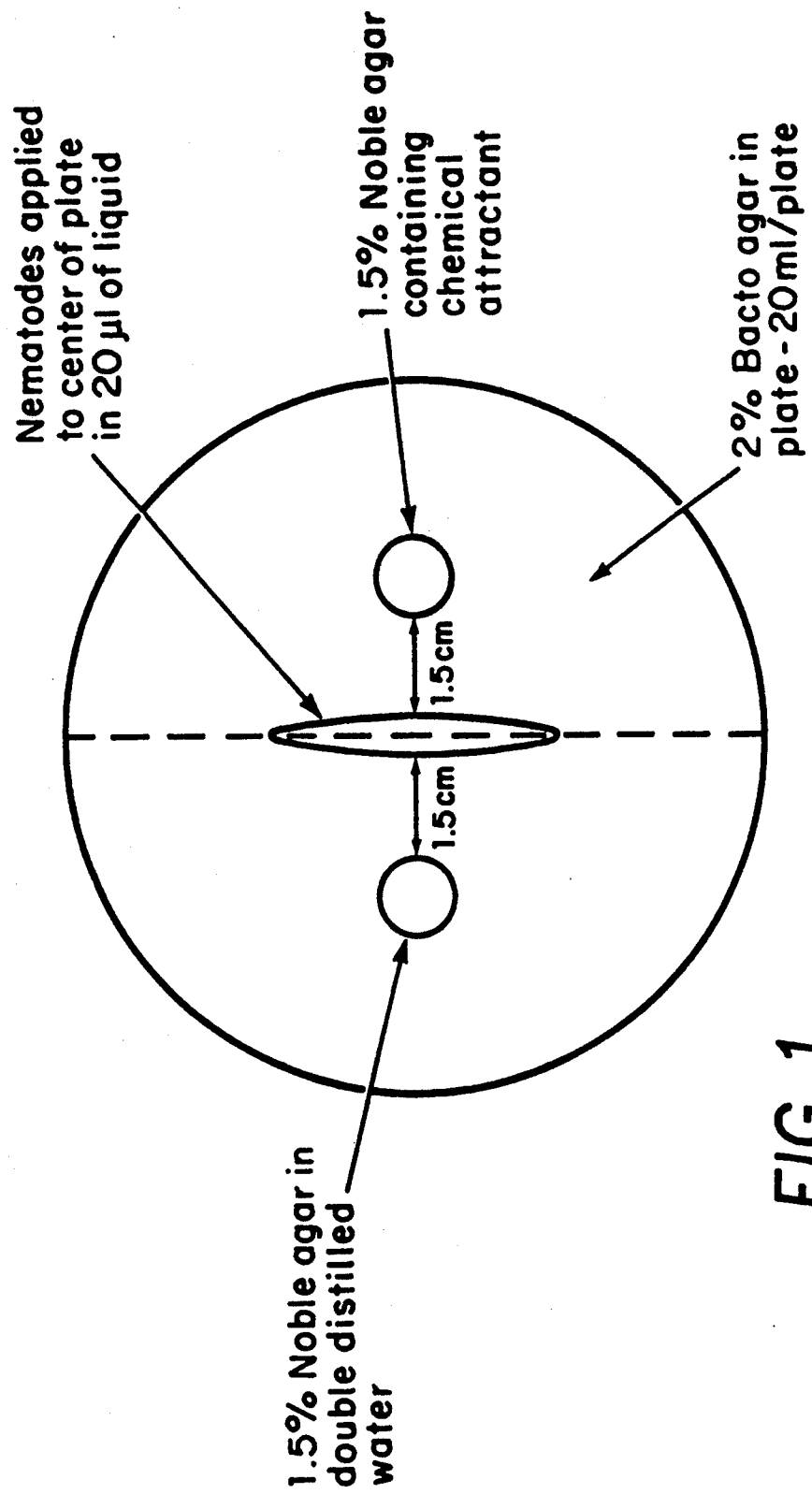
FIG. 1 is a top view of a device for an agar plate chemotaxis assay of the motility and viability of nematodes.

The approach of the invention, which provides an effective device and protocol for the in vitro testing of potential nematicidal and nematistatic agents, comprises treatment of nematodes with such agents, and assessing the effects of these agents on the vitality of the organisms using a chemotaxis assay device.

A. Preparation of nematodes

Parasitic nematodes are isolated from appropriate plant roots, e.g., *M. incognita* from tomato plants, and *M. javanica* and *M. hapla* from eggplants, as follows.

Nematode eggs are released from egg masses on infected roots using the technique of McClure et al., *Journal of Nematology* 5:230 (1973), which is incorporated herein by reference. Active second stage juveniles are harvested from the eggs, and stored at 10°–25° C., preferably 14°–16° C., in a solution of an antibiotic, typically streptomycin sulfate.

Prior to use, nematodes are warmed to room temperature, isolated, and washed with sterile water by centrifugation. Thereafter, suspensions of appropriate density are prepared, typically, 15,000–60,000 organisms per ml.

B. Treatment of Nematodes

Aliquots of the washed nematodes are added to suitable containers containing the particular nematicidal or nematistatic agents in appropriate concentrations. It is expected that those with ordinary skill in the art will, by experimentation, select ratios of numbers of nematodes to concentrations of test substances appropriate to elicit the maximum effects of such agents on the nematodes. Typically, about 25,000–30,000 nematodes in 0.5 ml. of solution are contacted with from 0 to 1 mg of suspected nematicidal or nematistatic agents.

Nematicidal or nematistatic agents are added to the treatment container in any suitable formulation: as a solution of the chemical, or in the form of carrier particles impregnated with a solution of the chemical.

Thereafter, nematodes are contacted with the chemical agents for a suitable period, typically 12–16 hours, at an appropriate temperature, typically room temperature, with shaking.

C. Chemotaxis Assay Device

1. Preparation of Chemattractant Source

Chemical chemattractants are intimately mixed with 0.5–3%, preferably 1.5%, tempered molten agar prepared with doubly-distilled water, and the molten mass poured into Petri dishes, typically 10×100 mm but other sizes may be appropriate. The concentration of such chemical chemattractants in the agar is selected according to the nature of the nematodes; typically, 5–50 mM concentrations of chemattractant salts can be employed. Once the agar is solidified, circular blocks (typically 10 mm diameter, but other sizes may be appropriate) are excised and stored.

The preferred chemattractants are salts of the alkaline earth metals. Most preferred are calcium chloride and calcium sulfate, although the chloride and sulfate salts of magnesium, manganese, and cobalt cations are also suitable.

Alternatively, thick filter paper (Whatman No. 3 MM) is saturated with chemical chemattractants in the appropriate concentration. Thereafter, the paper is air dried, and disks of the appropriate diameter excised and stored for use.

2. Preparation of Coated Solid Supports

Solid supports are coated with a thin layer of a ment, Petri dishes are thinly (typically, 1–5 mm, preferably 3 mm thick) coated with 2% Bacto agar. Other polymeric substrates include, but are not limited to any galactan, cross-linked dextran, allyl dextran, hydroxypropylated dextran, or silica gel.

It is an important aspect of this invention that the aforementioned coating has incorporated within it a chemical agent that stabilizes the assay. The term "stabilizes" is intended to mean a prevention of the reversibility of nematode movement, following chemattraction, that may be a problem in chemotaxis assays in which particular chemattractant salts are employed.

Stabilization agents comprise chloride and sulfate salts of monovalent alkali metals. The preferred monovalent alkali metals include, but are not limited to, sodium, potassium, and lithium cations, although cesium and rubidium ions are also suitable. The selection of the anion of the stabilizing salt is based upon the nature of the chemattractant salt employed. The anion in both cases should be the same.

The concentration of the stabilizing salt is based upon the concentration of the chemattractant salt gradient in the chemotaxis assay plate. For example, where the concentration of $CaCl_2$ in the aforementioned chemattractant block is 25 mM prior to gradient formation (see infra), the maximum concentration of calcium ions in the agar immediately adjacent to the block after gradient formation will be about 2.5 mM and that of chloride ion about 5.0 mM (see FIG. 4). Under these conditions, the concentration of NaCl as a stabilizing agent in the coating should be at least equal by the gradient, i.e., 5 mM, but most preferably twice that concentration is recommended. It is hypothesized, but the inventors do not intend to be bound by the hypothesis, that these concentrations of NaCl deliver chloride ion concentrations that effectively negate the chloride anion gradient created by the calcium chloride in the attractant block. It should be recalled that chloride ion gradients themselves are a repellent for *M. javanica* (Prot, supra). This provides an explanation for why only 5–10 mM sodium chloride need be incorporated into the aforementioned coating where the maximum chloride ion concentration adjacent to the chematractant block is 5 mM.

3. Establishing a Chemattractant Gradient

A circular block or disk containing the chemattractant is placed at an appropriate site on the surface of the aforementioned coated solid support. "Appropriate site" as used herein is intended to mean a point sufficiently near to the nematode application site that the chemattractant gradient (see infra) will overlap with the nematode application site. Typically, a 1.0 cm disk or block will be placed about 1.5 cm from the center of a 10 cm coated plate (see FIG. 1). Although more than one chemattractant block can be placed on a coated plate, it is preferred to use a single chemattractant block so as to avoid attraction for nematodes by competing gradients, which may produce ambiguous results.

Figure 4:
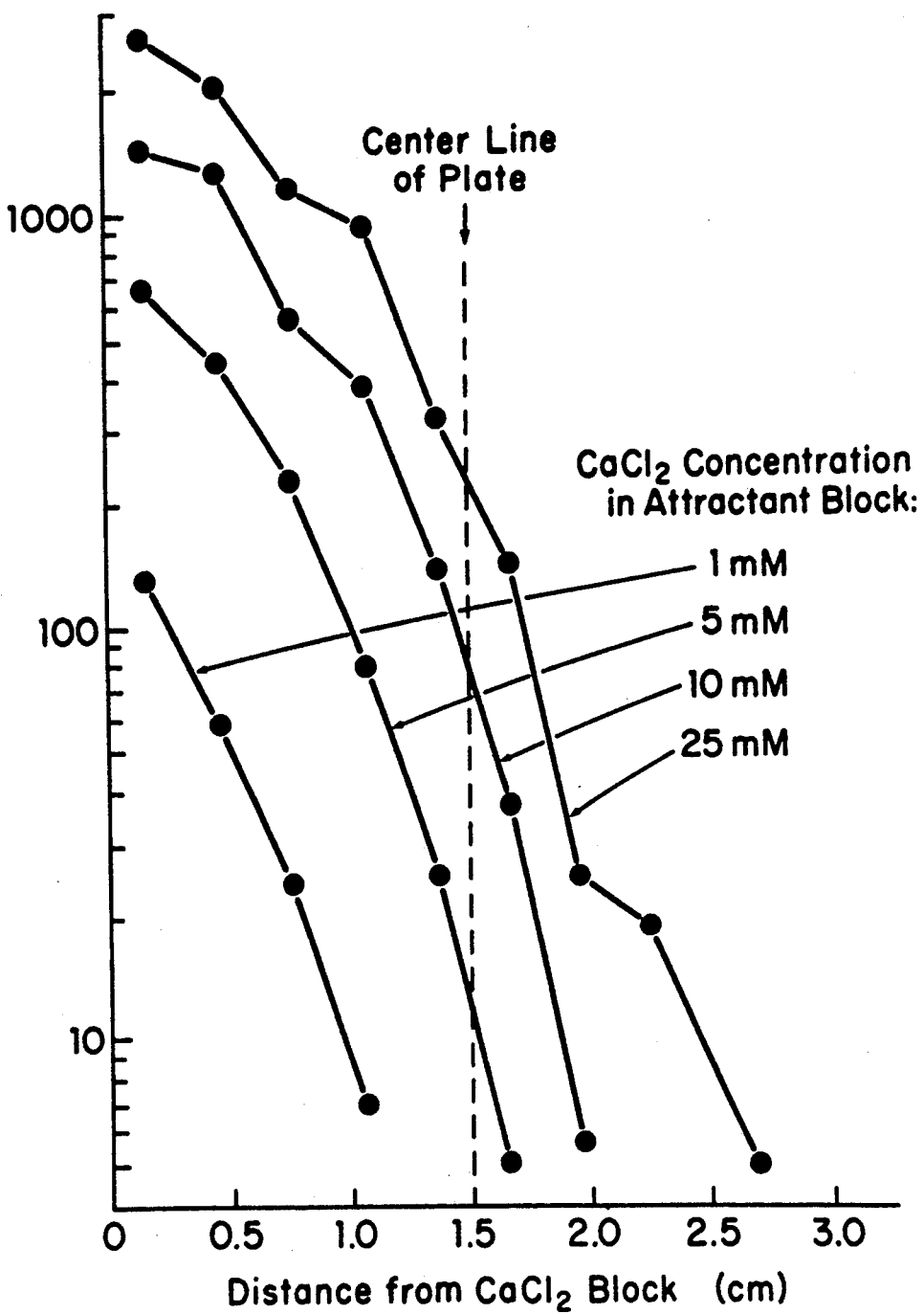
FIG. 4 is a graph depicting the concentration of calcium ions at various distances from the site of application of $CaCl_2$ on an agar chemotaxis assay plate.

The chemattractant block is contacted with the coated plate under conditions appropriate to establishing a chemattractant gradient. It is preferred that the contact be from 18 to 24 hours at room temperature, preferably 20 hours. As seen in FIG. 4 infra, starting with an initial $CaCl_2$ concentration in the chemattractant block of from 1 to 25 mM, linear gradients were formed within 20 hours.

4. Chemotaxis Assay

A small aliquot of a suspension of treated or untreated nematodes, typically 20ul, delivering 10–10,000, preferably 500–1,000, nematodes, is added to the aforementioned (3. supra) nematode application site on the assay plate.

After the liquid evaporates, the plates are incubated at room temperature, preferably in the dark so as to avoid the possible influences of lumattraction. Nematode movement is examined at intervals over a period of from 2 to 8 hours, preferably 4 to 6 hours.

Viability of treated nematodes is preferably assessed simply by (1) examining the general shift of population relative to the site of application of nematodes, and (2) counting the number of nematodes under the attractant block. A variety of means are available to assess nematode movement, and the inventors do not intend to be limited to any one method. Examples of suitable methods include, but are not limited to observation by the naked eye or by optical means.

Having now generally described the invention, the same will be more clearly understood by reference to the following examples, none of which are intended to be limiting unless so specified.

Example I relates to that aspect of the invention that comprises the chemotaxis assay itself.

Example II relates to that aspect of the invention that comprises treatment of nematodes with suspected nematicidal or nematistatic agents, followed by assessment of viability by the chemotaxis assay.

Example III relates to that aspect of the invention that comprises an assay for the formation of the $CaCl_2$ chemattractant gradient in coated plates following application of the disk or block containing the chemattractant.

All literature reference cited in these examples are incorporated into this application by reference.

EXAMPLE I

The Chemotaxis Assay

*M. incognita* was isolated from tomato plants, and *M. javanica* and *M. hapla* from eggplants. Eggs were released from egg masses on infected roots using the technique of McClure (supra). Second stage juveniles were obtained by placing the eggs on a wire mesh screen containing six layers of Kimwipes ® and incubating in a Petri dish containing a solution of 1% (w/v) streptomycin sulfate. Juveniles were harvested every two days and refiltered through Kimwipes ® as above. The nematodes were stored at 15° C. in a solution of 1% streptomycin sulfate. Prior to use for chemotaxis, the nematodes were warmed to room temperature and isolated by centrifugation (2,000× g for 5 minutes). After washing the organisms once with sterile distilled water, they were adjusted to a concentration of about 25,000 nematodes per ml.

The chemotaxis assay was set up as follows. $CaCl_{12}$, 25 mM, was mixed with 25 ml of molten, tempered (44° C.) 1.5% Noble agar prepared with distilled water, and the mix poured into a 15×100 mm Petri plate. Once the agar solidified, 1.0 cm disks or blocks were excised and placed on a 15×100 mm Petri plate containing 20 ml of Bacto agar (Difco), made up to contain 5-10 mM NaCl, as shown in FIG. 1. Each Bacto agar plate contained one control water agar block and one chemattractant block, each placed 1.5 cm from the midline of the plate. The plate was incubated at room temperature for 20 hours to allow a chemical gradient to be formed (cf., Example 2 and FIG. 4 infra).

The chemotaxis assay was initiated by placing approximately 500 nematodes in 20 ul along the midline of the assay plate (FIG. 1). The assays were performed in triplicate.

Figure 2:
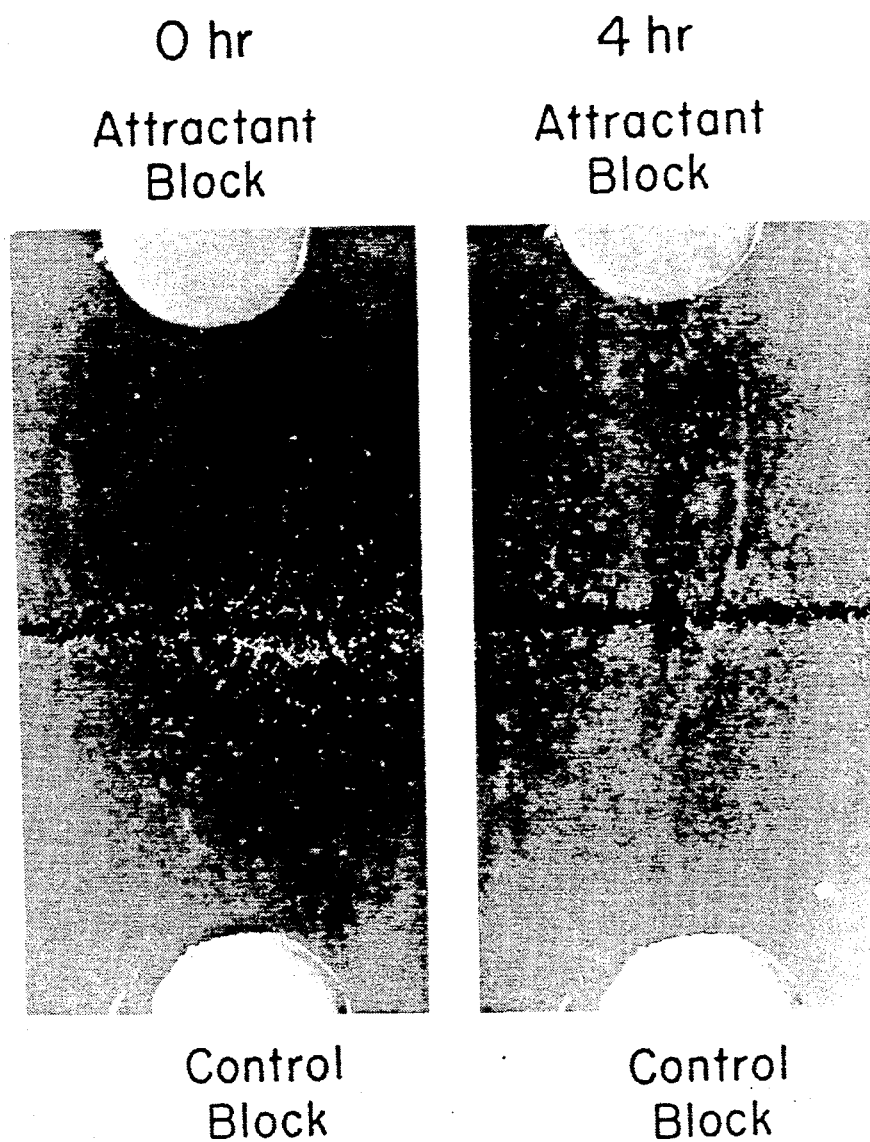
FIG. 2 is a photograph of the movement of nematodes toward a chemattractant ($CaCl_2$) in an agar plate chemotaxis is assay.
Figure 3:
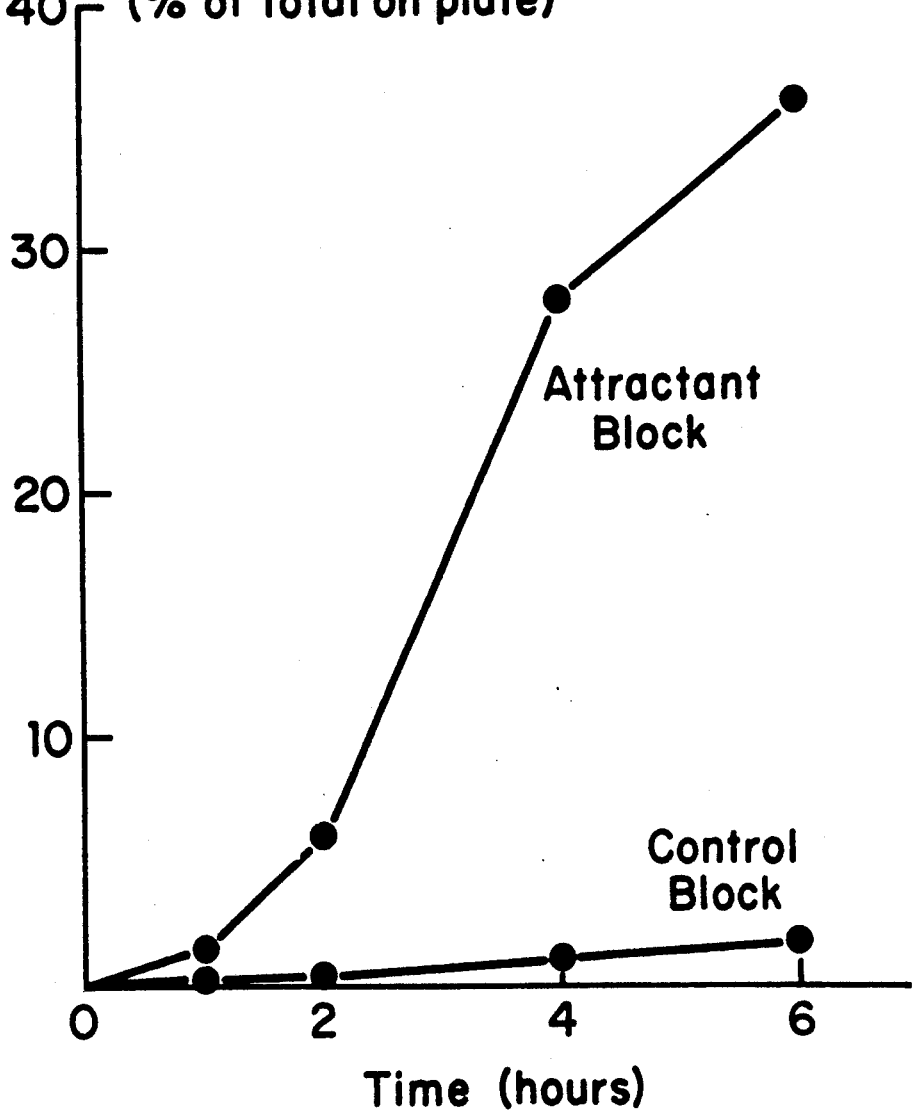
FIG. 3 is a graph depicting the number of nematodes accumulating under a $CaCl_2$ chemattractant block as a function of time.

After the liquid had evaporated, plates were incubated in the dark at room temperature, and nematode movement examined over six hours. Chemattraction, as well as viability, was assessed by (1) examining the general shift of the population relative to the midline and to the chemattractant agar block and the control water agar block (FIG. 2), and (2) by counting the number of nematodes under the attractant and control agar blocks (FIG. 3).

EXAMPLE II

Effect of Pretreatment of Nematodes With Nematicidal Agents on the Chemotaxis Assay Aldicarb (450 ug of the active component of TEMIK 15G$^R$, Union Carbide, in a gypsum carrier (15% aldicarb plus 85% inert carrier)) was dispensed into 1.5 ml Eppendorf centrifuge tubes. A control tube contained gypsum granules without aldicarb.

Oxamyl (from 0 to 5 ul of a 23 ug/ml water solution of Vydate LR, DuPont) was dispensed into 1.5 ml Eppendorf tubes.

To each tube was added 25,000-30,000 nematodes suspended in 0.5 ml of water. The tubes were then incubated at room temperature for 16 hours on a rotator.

Bacto agar (2%) plates made up in 10 mM NaCl, with 25 mM $CaCl_2$ attractant blocks were prepared as in Example I supra. Gradients were formed over 20 hours.

Aliquots (20 ul) of the treated nematode suspension were added to triplicate chemotaxis assay plates, as in Example I supra. Plates were incubated in the dark at room temperature, and nematode movement was assessed at 2, 4, and 6 hours. The results are shown in Table I.

It is clear from the results shown in Table I that, in the water and gypsum controls, there was a rapid movement of large numbers of nematodes through $CaCl_2$ gradients, with the peak occurring at 4 hours. In contrast, nematodes treated with aldicarb or oxamyl essentially failed to exhibit significant motility, even as late as six hours.

TABLE I

| Chemotaxis Assay of Nematodes after Treatment with Aldicarb and Oxamyl* | | | |
|---|---|---|---|
| Treatment | 2 hrs | 4 hrs | 6 hrs |
| Water control | 173(7)** | 400(37) | 193(29) |
| Gypsum control | 149(106) | 233(68) | 154(37) |
| Aldicarb | 0 | 0 | 0 |
| Oxamyl (2.3 ppm) | 3 | 33(1) | 30(0) |
| Oxamyl (4.6 ppm) | 0 | 4(1) | 11(2) |

*The values represent the approximate numbers of organisms under the chemattractant blocks
**The values in parentheses represent water agar block controls.

EXAMPLE III

Calcium Diffusion Assay

Agar blocks (1.0 cm diameter) containing various concentrations of $CaCl_2$ and supplemented with $^{45}CaCl_2$ (New England Nuclear Corporation) at a known specific activity were placed in the standard chemotaxis agar plate containing 10 mM NaCl, as shown in Example I and FIG. 1. The plates were incubated for 20 hours under standard conditions to establish the $CaCl_2$ gradient.

Agar slices were removed from various positions on the agar plate, and placed in scintillation fluid (Aquasol) to determine the amount of radioactivity. The calcium concentration at each position on the plate was determined by dividing the counts in the agar slices at a particular position on the plate by the $CaCl_2$ block that had been placed on the plate. This ratio was divided by the specific activity of the radioactive $CaCl_2$ to obtain the molar concentration of $CaCl_2$ at each position on the agar plate. The molar concentrations of chloride ions are, of course, twice those of the $CaCl_2$.

The results, depicted in FIG. 4, demonstrate the linearity of the $CaCl_2$ gradient emanating from the chemattractant block and encompassing the center line of the plate, i.e., the site of application of the nematodes.

Thus, the nematodes encountered the chloride ion component of the chemattractant at all times, beginning with the moment of their application to the chemotaxis assay plate.

The minimum effective concentration of $CaCl_2$ to attract Meloidogyne nematodes was 5 mM in the chemattractant block initially. Following 20 hours of gradient formation, the $Ca^{2+}$ concentration in the center of the plate where the nematodes were applied was about 15 uM (of., FIG. 4). Thus, the threshold level for attraction of Meloidogyne to calcium appears to be approximately 15 uM.

What is new and desired to be covered by letter patents are:

1. A device for the detection of nematode vitality comprising:

(a) a solid surface having a coating, said coatign comprising a mixture of a gellable polymeric substrate and an assay stabilizing salt;

(b) said coating also containing, at particular areas, concentration gradients of a chemaatractant inorganic salt, wherein the anions of said assay stabilizing salt and of said chemattractant inorganic salt are identical.

2. The device of claim 1 wherein said solid surface comprises a Petri dish.

3. The device of claim 2 wherein said Petri dish is composed of glass.

4. The device of claim 2 wherein said Petri dish is composed of plastic.

5. The device of claim 1 wherein said solid surface comprises a plate.

6. The device of claim 5 wherein said plate is composed of glass.

7. The device of claim 5 wherein said plate is composed of a plastic.

8. The device of claim 1 wherein said gellable polymeric substrate is selected from the group consisting of agar, galactan, cross-linked dextran, hydroxypropylated dextran and silica gel.

9. The device of claim 1 wherein said stabilizing salt is selected from the group consisting of chlorides salts of sodium, potassium, lithium, rubidium and cesium.

10. The device of claim 9 wherein said stablizing salt comprises sodium chloride.

11. The device of claim 1 wherein said stabilizing salt is selected from the group consisting of sulfate salts of sodium, potassium, lithium, rubidium, and cesium.

12. The device of claim 11 wherein said stabilizing salt comprises sodium sulfate.

13. The device of claim 1 wherein said chematratant inorganic salt comprises an alkaline earth metal salt.

14. The device of claim 13 wherein said chematractant salt comprises a divalent cation linked to an anion identical to the anion of said assay stabilizing salt.

15. The device of claim 1 wherein said chemattractant salt comprises chloride salts of divalent cations selected from the group consisting of beryllium, magnesium, calcium, strontium, barium, cobalt and manganese.

16. The device of claim 13 wherein the chematractant salt is calcium chloride.

17. The device of claim 13 wherein said chematractant salt comprises sulfate salts of divalent cations selected from the group consisting of beryllium, magnesium, calcium, strontium, barium, cobalt, and manganese.

18. The device of claim 17 wherein aid chematractant salt comprises calcium sulfate.

* * * * *